(12) United States Patent
Popovic et al.

(10) Patent No.: US 12,376,738 B2
(45) Date of Patent: Aug. 5, 2025

(54) IMAGE GUIDED ROBOTIC SYSTEM FOR TUMOR ASPIRATION

(71) Applicant: KONINKLIJKE PHILIPS N.V., Eindhoven (NL)

(72) Inventors: Aleksandra Popovic, Boston, MA (US); David Paul Noonan, New York, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 456 days.

(21) Appl. No.: 17/859,052

(22) Filed: Jul. 7, 2022

(65) Prior Publication Data

US 2022/0331027 A1 Oct. 20, 2022

Related U.S. Application Data

(63) Continuation of application No. 16/086,907, filed as application No. PCT/EP2017/057704 on Mar. 31, 2017, now Pat. No. 11,399,901.

(Continued)

(51) Int. Cl.
*A61B 1/00* (2006.01)
*A61B 1/018* (2006.01)
(Continued)

(52) U.S. Cl.
CPC ............ *A61B 1/04* (2013.01); *A61B 1/00009* (2013.01); *A61B 1/00087* (2013.01); *A61B 1/00094* (2013.01); *A61B 1/00149* (2013.01); *A61B 1/0016* (2013.01); *A61B 1/018* (2013.01); *A61B 5/06* (2013.01); *A61B 17/22* (2013.01); *A61B 34/30* (2016.02); *A61B 34/32* (2016.02); *G16H 20/40* (2018.01); *G16H 30/20* (2018.01); *G16H 40/63* (2018.01); *A61B 1/00039* (2013.01); *A61B 1/00045* (2013.01); *A61B 2017/0034* (2013.01); *A61B 2017/22079* (2013.01); *A61B 2018/00982* (2013.01);
(Continued)

(58) Field of Classification Search
CPC ............ A61B 1/00009; A61B 1/00094; A61B 1/00149; A61B 1/0016; A61B 1/018; A61B 17/22; A61B 34/30; A61B 2034/2065; A61B 2034/301; A61B 2017/22079; G16H 40/63
See application file for complete search history.

(56) References Cited

U.S. PATENT DOCUMENTS

| 5,972,012 A | 10/1999 | Ream | |
|---|---|---|---|
| 6,997,926 B2 * | 2/2006 | Gellman | ............ A61B 18/082 606/46 |

(Continued)

FOREIGN PATENT DOCUMENTS

| JP | 2001104335 | 4/2001 |
|---|---|---|
| WO | 2015118422 A1 | 8/2015 |

*Primary Examiner* — Anh Tuan T Nguyen
*Assistant Examiner* — Rynae E Boler

(57) ABSTRACT

A robot controller (515) includes a first input (502) configured to receive images (524) from an imaging device for a region of interest. A target identification device (516) is configured to identify a target region in the images. A control system (517) is coupled to a robotically controlled treatment device to generate control signals to control the treatment device to treat the target region when the treatment device is positioned corresponding to the target region.

20 Claims, 5 Drawing Sheets

Related U.S. Application Data

(60) Provisional application No. 62/315,915, filed on Mar. 31, 2016.

(51) Int. Cl.
| | |
|---|---|
| *A61B 1/04* | (2006.01) |
| *A61B 5/06* | (2006.01) |
| *A61B 17/22* | (2006.01) |
| *A61B 34/30* | (2016.01) |
| *A61B 34/32* | (2016.01) |
| *G16H 20/40* | (2018.01) |
| *G16H 30/20* | (2018.01) |
| *G16H 40/63* | (2018.01) |
| *A61B 17/00* | (2006.01) |
| *A61B 18/00* | (2006.01) |
| *A61B 34/20* | (2016.01) |
| *A61B 90/00* | (2016.01) |
| *A61M 25/01* | (2006.01) |

(52) U.S. Cl.
CPC . *A61B 2034/2065* (2016.02); *A61B 2034/301* (2016.02); *A61B 2090/364* (2016.02); *A61B 2217/005* (2013.01); *A61B 2218/007* (2013.01); *A61M 25/0116* (2013.01)

(56) References Cited

U.S. PATENT DOCUMENTS

| | | | |
|---|---|---|---|
| 8,934,003 | B2 | 1/2015 | Popovic |
| 9,554,797 | B2 * | 1/2017 | Swope .................. A61F 5/0086 |
| 9,603,666 | B2 * | 3/2017 | Elhawary .............. A61B 1/0016 |
| 9,782,198 | B2 * | 10/2017 | Elhawary ............... A61B 34/20 |
| 2004/0102804 | A1 * | 5/2004 | Chin ................ A61B 17/00008 |
| | | | 606/151 |
| 2007/0005002 | A1 | 1/2007 | Millman |
| 2012/0310110 | A1 * | 12/2012 | Rhad ................... A61B 10/0266 |
| | | | 600/567 |
| 2014/0142422 | A1 * | 5/2014 | Manzke .................... A61B 8/12 |
| | | | 600/424 |
| 2014/0343416 | A1 | 11/2014 | Panescu |
| 2015/0080652 | A1 | 3/2015 | Staples |
| 2015/0133961 | A1 | 5/2015 | Uchida |
| 2015/0223832 | A1 | 8/2015 | Swaney |
| 2015/0297313 | A1 | 10/2015 | Reiter |
| 2016/0045269 | A1 | 2/2016 | Elhawary |
| 2016/0100854 | A1 * | 4/2016 | Hyde ................... A61B 90/361 |
| | | | 600/309 |
| 2016/0196652 | A1 * | 7/2016 | Ye ........................... G06T 7/262 |
| | | | 382/103 |
| 2016/0360947 | A1 | 12/2016 | Ida |
| 2016/0367120 | A1 * | 12/2016 | Dupont .............. A61B 1/00082 |
| 2017/0196643 | A1 | 7/2017 | Popovic |
| 2018/0193102 | A1 | 7/2018 | Inoue |

\* cited by examiner

IMAGE GUIDED ROBOTIC SYSTEM FOR TUMOR ASPIRATION

CROSS-REFERENCE TO PRIOR APPLICATIONS

This application is a Continuation of application Ser. No. 16/086,907, filed on Sep. 20, 2018, which is the U.S. National Phase application under 35 U.S.C. § 371 of International Application No. PCT/EP2017/057704, filed on Mar. 31, 2017, which claims the benefit of U.S. Provisional Patent Application Ser. No. 62/315,915, filed on Mar. 31, 2016. These applications are hereby incorporated by reference herein.

BACKGROUND

Technical Field

This disclosure relates to medical instruments and more particularly to systems and methods for robotically treating (e.g., aspirating) a cyst, tumor or other tissue in medical applications.

Description of the Related Art

A colloid cyst is a gelatinous formation that forms in the ventricles of the brain (commonly the third ventricle). Due to its location close to critical structures, various complications can be caused including swelling of the brain or a rupture of ventricular structures. Colloid cysts are treated with open surgery or using minimally invasive techniques for endoscopic cyst aspiration.

The minimally invasive approach includes insertion of a rigid endoscope through a burr hole in the skull. The endoscope has at least one instrument channel through which an aspiration/suction catheter is introduced. The surgeon introduces the endoscope in the third ventricle and manually guides it towards the cyst. Once the surgeon estimates that the endoscope and the suction catheter are close enough to the cyst, the suction is initiated. This process is repeated until the cyst is retrieved through the catheter.

A similar endoscopic approach can be employed to retrieve heart tumors or blood clots from the heart ventricles. In general surgery, this technique is used for removal of cysts, abscesses or tumors for kidneys, livers, and other organs. Additionally, this approach could be employed with other technologies, e.g., laser cutting, ablation (e.g., RF or microwave electrodes), cauterizing, electroporation, histotripsy, high intensity focused ultrasound, etc.

SUMMARY

In accordance with the present principles, a robot controller includes a first input configured to receive images from an imaging device for a region of interest. A target identification device is configured to identify at least one target region in the images. A control system is coupled to a robotically controlled treatment device to generate control signals to control the treatment device to treat the at least one target region when the treatment device is positioned corresponding to the at least one target region.

A treatment system includes an aspiration device and a robot system capable of being coupled to the aspiration device. The robot system includes at least one joint and at least two links to limit motion of the aspiration device at an insertion point into a subject. A control system is coupled to the robot system to control motion of the robot system and the aspiration device to permit access to an internal target within the subject to permit bursts of aspiration across the target based upon the motion of the robot system.

A method for treatment of tissue includes inserting an endoscope with a treatment device into an area of interest, the endoscope being coupled to a robot system; identifying a target; tracking the target using image-based tracking; aligning the endoscope and the treatment device with the target such that the endoscope is pivoted around an insertion point into a subject; measuring the target in an endoscope view to determine a position of the treatment device relative to the target; positioning the treatment device at a predefined position from the target for treatment; and treating the target with one or more bursts of the treatment device as controlled by a control system.

These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein.

DETAILED DESCRIPTION OF EMBODIMENTS

Figure 1:
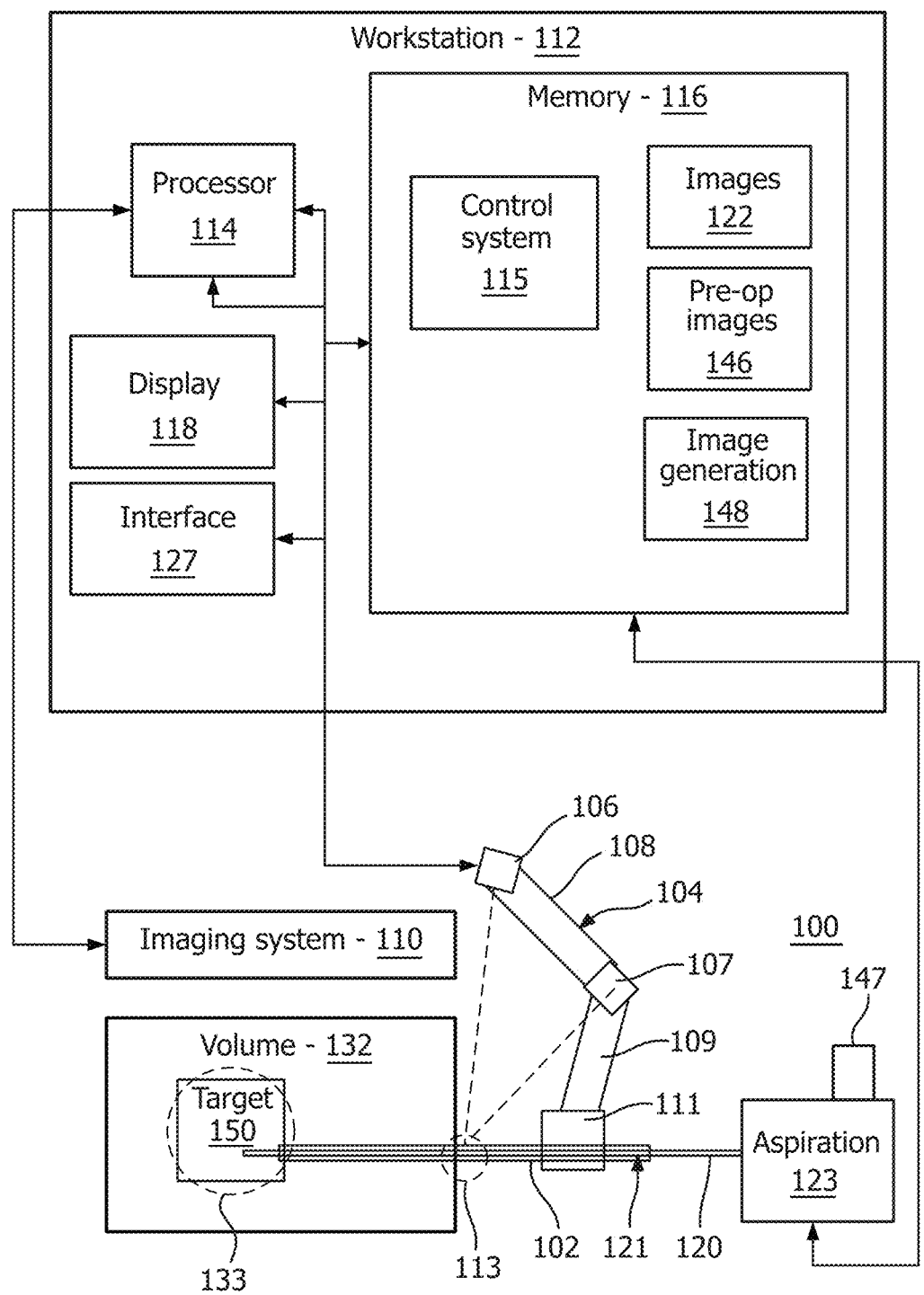
FIG. 1 is a block/flow diagram showing an aspiration system in accordance with one embodiment.

In accordance with the present principles, systems and methods are provided for image guided positioning of an endoscope and image guided deployment thereof for aspiration to remove cysts, blood clots or other unwanted formations in organs (e.g., a colloid cyst or heart tumor). The image guided methods assure an efficient motion of the endoscope to reduce tissue damage and promote efficient aspiration control to reduce the amount of fluid removed or the removal of unwanted tissue.

Handling of an endoscope in surgical procedures and mapping the endoscope images to motion of the endoscope is difficult. Furthermore, a fulcrum effect at an insertion point inverts mapping of the tip position to the endoscope position outside of the body. This can result in repeated attempts to position the endoscope towards the target, which can cause tissue damage or ruptures, especially in cases where the fulcrum point of the scope is far from the aspiration site, such as, e.g., in the skull for neurosurgery or ribs for cardiac surgery. In these cases, the endoscope motion may cause damage to tissue. Thus, the amount of motion of the endoscope should be reduced to a minimal path and a single attempt.

Deployment of suction is employed in an aspiration procedure. If an excessive amount of fluid is removed from the organ or area, fluid may need to be recirculated back through a catheter into the body. This can increase the risk of infection. Thus, the suction should preferably be deployed in a small number of short bursts to avoid excessive removal of fluid.

The present principles employ an actuated robotic system with at least one joint and two links. In one embodiment, the robotic system implements a mechanical remote center of motion to limit the motion of a robot end-effector (e.g., distal end of the robot that performs a function (e.g., a tip of an endoscope, the combination of endoscope and the suction device, etc.)) to rotation around an insertion/fulcrum point. For example, the robot may employ two revolute joints with intersecting axes and a distal link with an end-effector (e.g., endoscope and/or aspiration catheter) also intersecting with revolute axes. This can be implemented with robot links in the shape of arcs. A third degree of freedom can be added to permit translation of the end-effector along the third axis. An endoscope employed in clinical practice may be attached to a distal end of the robot, with at least one instrument channel and an aspiration catheter inserted through that channel. A control system controls the robot and the aspiration mechanism and receives image data from the endoscope.

In one embodiment, a remote center of motion (RCM) is employed for the robot. RCM is a fixed point in space about which a part of a robot system can rotate and is located a distance from any joint. RCM controls action of a robot to constrain motion at a device center of a device being manipulated by the robot. RCM can be controlled by mechanical design or through software constraints. RCM software is realized through coordinated joint control of a multiple degree of freedom robot. RCM software automates robot control through issued commands from a controller or control system to constrain robot motion (control joint motion) and maintain RCM or provide other motion capabilities of constraints.

In one illustrative method, an endoscope with the aspiration catheter is inserted into an area of interest, e.g., a third ventricle of the brain. The endoscope is directly or indirectly coupled to the robot, for example, the endoscope is aligned along the third axis intersecting rotational axes of the RCM mechanism. A target (e.g., a colloid cyst) is identified by a surgeon and communicated to a control system (e.g., observed in the endoscope or pre-operative images and marked on the image using a mouse click or a similar user interface). The control system performs image-based tracking of the cyst in the endoscope image stream using methods, such as, e.g., optical flow or normalized cross-correlation. The surgeon activates the endoscope positioning and the robot performs visual servoing to align the endoscope and the aspiration catheter with the target. This can be performed using uncalibrated visual servoing. The endoscope is pivoted around the insertion point (e.g., skull or ribs), and the axis is aligned with the target.

Once the endoscope is aligned, the size of the target (e.g., a cyst) is measured in the endoscope view. This can be done, for example, by fitting a circle around the edges of the cyst. A similar circle or a sphere is fitted on the preoperative cyst image, e.g., a magnetic resonance image (MRI). Magnification is defined as m=radius of cyst in endoscope view (in pixels)/radius of cyst from preoperative image (in mm). Once the magnification is known, the distance between the endoscope tip (and aspiration catheter) and the cyst can be computed as: distance=m*f where f is the focal length of the endoscope lens. In an alternative embodiment, if the focal length of the endoscope is not known, the endoscope can be moved by a known distance towards the cyst. The change of magnification number can be related to known motion to calibrate for the focal length.

Once the distance is known, the endoscope is advanced towards the cyst to position the aspiration catheter (or therapy device) and the cyst at a predefined distance for optimal operation (defined by the therapy device). As the endoscope reaches the desired distance, aspiration is initiated for a minimal amount of time defined as distance/speed of aspiration. These steps may be repeated until the cyst is successfully retrieved.

In other embodiments, the endoscope system may be implemented as a snake-like robot with at least one joint inserted into the body. In a preferred embodiment, two concentric joints may be controlled by two motors implementing yaw and pitch motion of the endoscope tip. These two joints can be aligned with a structure inside the body, such as a third ventricle wall or heart wall. The device further implements an endoscope channel for suction. The control of the device is the same as described, as the joints are controlled as a local remote center of motion (RCM) in the same fashion as a RCM robot. This device can be combined with an RCM robot in yet another embodiment.

It should be understood that the present invention will be described in terms of medical instruments; however, the teachings of the present invention are much broader and are applicable to any robot controlled instruments. In some embodiments, the present principles are employed in tracking or analyzing complex biological or mechanical systems. In particular, the present principles are applicable to internal tracking and operating procedures of biological systems and procedures in all areas of the body such as the lungs, brain, heart, gastro-intestinal tract, excretory organs, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk—read only memory (CD-ROM), compact disk—read/write (CD-R/W), Blu-Ray™ and DVD.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

It will also be understood that when an element such as an element, region or material is referred to as being "on" or "over" another element, it can be directly on the other element or intervening elements may also be present. In contrast, when an element is referred to as being "directly on" or "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Referring now to the drawings in which like numerals represent the same or similar elements and initially to FIG. 1, a system 100 for robotic aspiration of tissue in a live subject is illustratively shown in accordance with one embodiment. System 100 may include a workstation or console 112 from which a procedure is supervised and/or managed. Workstation 112 preferably includes one or more processors 114 and memory 116 for storing programs and applications. Memory 116 may store a control system 115 configured to control movement and programming of an actuated robot system 104 in accordance with user input and/or feedback provided from one or more inputs.

While the robot system 104 includes, at a minimum one joint and two links, preferably, the robot system 104 includes at least two joints 106, 107 and two links 108, 109. In one embodiment, the robotic system 104 implements a mechanical remote center of motion (RCM) to limit the motion of a robot to rotation around an insertion/fulcrum point 113. The robot system 104 may employ two revolute joints (106, 107) with intersecting axes and a distal link 111 also intersecting with revolute axes. This can be implemented with robot links in the shape of arcs. A third degree of freedom can be added to permit translation of the link 111 (and any instrument held or attached to the link 111) and the along a third axis.

Figure 2:
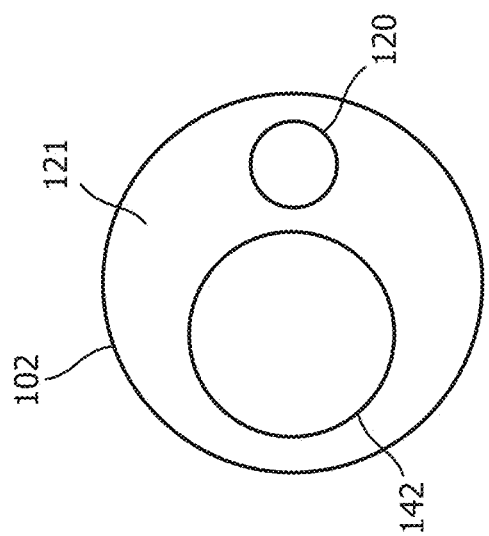
FIG. 2 is a cross-sectional view of an endoscope showing an aspiration catheter in an instrument channel in accordance with one embodiment.

An endoscope 102 may be employed and attached or grasped to or at a distal end (distal link 111) of the robot system 104. The endoscope 102 includes at least one instrument channel 121 and a treatment device (e.g., an aspiration catheter) 120 inserted through that channel 121 (FIG. 2). The control system 115 controls the robot system 104 and an aspiration system or module 123 (e.g., coupled to the aspiration catheter 120) and receives image data from the endoscope 102.

The endoscope 102 with the treatment device (aspiration catheter) 120 is inserted into an area of interest, e.g., the third ventricle of the brain. The endoscope 102 is attached to the distal link 111 of the robot system 104. A target 150 (e.g., a colloid cyst) is identified by a surgeon in endoscope images 122 generated by the endoscope 102 (e.g., an imaging device provided by or through the endoscope 102) and rendered on a display 118. The images 122 may be marked using a mouse click or a similar user interface 127. The control system 115 performs image-based tracking of the target 150 in the endoscope image stream using methods, such as, e.g., optical flow or normalized cross-correlation. The surgeon activates the endoscope positioning (with e.g., a trigger event). The robot system 104 responds to the trigger event (e.g., pressing a button, throwing a switch, etc.) and performs visual servoing to align the endoscope 102 and the aspiration catheter 120 with the target 150. This can be performed using uncalibrated visual servoing and may include aligning a longitudinal axis of the treatment device 120 (aspirational catheter) with a point on the target 150. The endoscope 102 is pivoted around the insertion point (e.g., skull or ribs) and the axis is aligned with the target 150.

Once the endoscope 102 is aligned, the size of the target 150 is measured in an endoscope view by fitting a circle or other shape or boundary 133 around the edges of the target 150 (e.g., cyst). A similar circle or a sphere is fitted on a preoperative image 146, e.g., a magnetic resonance image (MRI), of the target 150.

Magnification is defined as m=radius of the target 150 in the endoscope view (in pixels)/radius of the target 150 from preoperative image 146 (in mm or equivalent). Once the magnification is known, the distance between the endoscope tip (and aspiration catheter 120) and the target 150 can be computed as: distance=m*f where f is the focal length of the endoscope lens. In an alternative embodiment, if the focal length of the endoscope 102 is not known, the endoscope 102 can be moved by a known distance towards the target 150. The change of magnification number can be related to known motion to calibrate for the focal length.

The endoscope 102 can be automatically advanced towards the target 150 to reduce a distance between the aspiration catheter 120 and the target 150 to a predefined distance for optimal aspiration. The optimal aspiration distance/time is computed by the control system 115. The aspiration system 123 may be programmed to compute and/or control the type of aspiration, the duration, pulse width, pressure differential etc. in accordance with a surgical plan or based on feedback from images or other components of the system 100. As the endoscope 102 reaches the desired distance, aspiration is initiated for a minimal amount of time defined as distance/speed of aspiration. These steps may be repeated until the target 150 (e.g., cyst) is successfully retrieved/drained. With each iteration or pass of the automatic deployment, short bursts of aspiration may be performed as the target is engaged (e.g., based on images and knowledge of how far the robot and thus the aspiration device are from the target) until the target is removed.

The aspiration system or module 123 may include components in memory for storing control points and aspiration cycles. The aspiration system 123 includes a vacuum pump 147 or other device to create and control suction in the aspiration catheter 120.

In one embodiment, workstation 112 includes an image generation module 148 configured to receive image feedback from the endoscope 102. The image generation module 148 can generate computer or user generated boundaries 133 in the images. These boundaries or shapes 133 may be overlaid on images 122, 146 (e.g., in-situ images, preoperative images or both). Workstation 112 includes the display 118 for viewing the images 122, 146 of the subject (patient) or volume 132 and may include the images 122,146 with overlays or other renderings. Display 118 may also permit a user to interact with the workstation 112 and its components and functions, or any other element within the system 100. This is further facilitated by the interface 127 which may include a keyboard, mouse, a joystick, a haptic device, or any other peripheral or control to permit user feedback from and interaction with the workstation 112.

The robot system 104 preferably includes image guided positioning of the endoscope 102 and image guided deployment of the aspiration catheter 120 to remove cysts, blood clots or other unwanted formations in organs (e.g., colloid cyst or heart tumor). The image guided methods assure an efficient motion of the endoscope and reduce tissue damage. Efficient aspiration control by aspiration system 123 reduces the amount of fluid removed from the unwanted formation. An imaging system 110 may or may not be present for obtaining preoperative images (e.g., MRI, etc.).

Referring to FIG. 2, a cross-sectional view of the endoscope 102 is illustratively shown in accordance with one embodiment. The endoscope 102 includes at least one instrument channel 121. The aspiration catheter 120 is inserted through the channel 121. A camera 142 or other imaging device may also be disposed within the same or different instrument channel 121.

Figure 3:
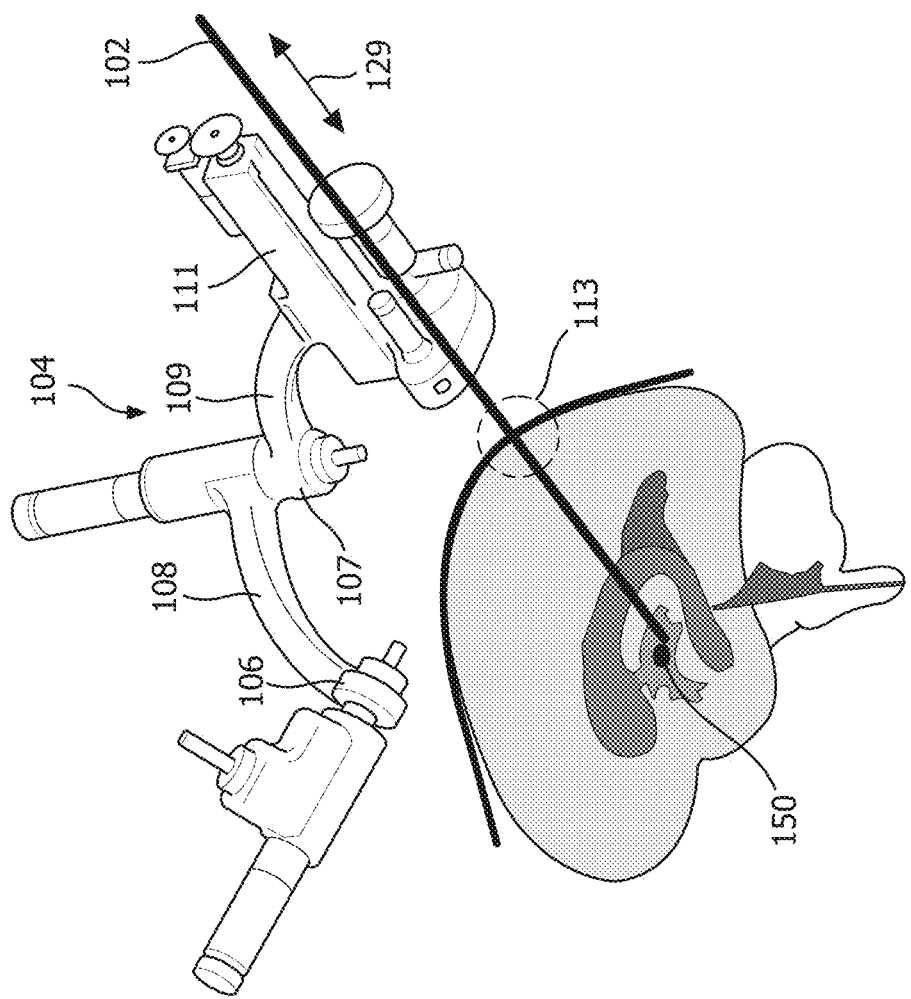
FIG. 3 is a diagram showing a robot system with target alignment of an endoscope/aspiration device in accordance with one embodiment.

Referring to FIG. 3, the robot system 104 is shown in greater detail. The robot system 104 is actuated with at least one joint and two links, but preferably with two joints 106, 107 and two links 108, 109. In one embodiment, the robotic system 104 implements a mechanical remote center of motion (RCM) to limit the motion of a robot end-effector (e.g., endoscope device 102 or treatment device 120) to rotation around an insertion/fulcrum point 113. The robot system 104 may employ two revolute joints (106, 107) with intersecting axes and the distal link 111 with the end-effector also intersecting with revolute axes. The intersecting axes of the joints 106, 107 and the end-effector (e.g., endoscope device 102 or treatment device 120) intersect at point 113. The robot links 108, 109 may be in the shape of arcs. A third degree of freedom can be added to permit translation of the end-effector (e.g., endoscope device 102 or treatment device 120) along a third axis 129. The endoscope 102 may be secured by the distal link 111 with at least one instrument channel to receive the aspiration catheter (120) inserted through the channel of the endoscope 102.

Figure 4:
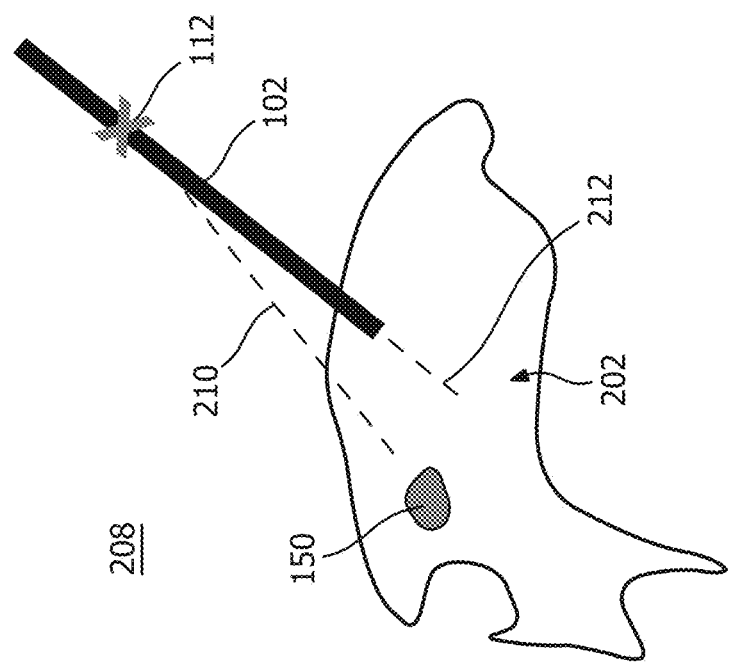
FIG. 4 is a diagram showing a process for target alignment of an endoscope/aspiration device in accordance with another embodiment.

Referring to FIG. 4, the endoscope 102 with the aspiration catheter (120) is inserted into an area of interest 202, e.g., a third ventricle of the brain. The endoscope 102 is attached to the distal link 111 (FIG. 3) of the robot system 104. A target 150 (e.g., colloid cyst) is identified by the surgeon in endoscope image 208 and communicated to the control system, for example, by the surgeon marking the image using a mouse click or a similar user interface. Image-based tracking of the target 150 is performed in an endoscope image stream using, e.g., optical flow or normalized cross-correlation. The user/surgeon activates an endoscope positioning function to initiate visual servoing of the robot system 104 to align the endoscope 102 and the aspiration catheter 120 along an axis 210 of the target 150 from an axis of insertion 212. This may be performed using uncalibrated visual servoing. The endoscope 102 is pivoted around the insertion point 113 and the axis of the endoscope 102 or device 120 is aligned with the target 150.

Once aligned, the endoscope 102 may be employed to measure the size of the target 150 (e.g., cyst) in the endoscope view. Magnification is determined, and a distance between the endoscope tip (and aspiration catheter) and the cyst can be computed. In alternative embodiment, if the focal length of the endoscope is not known, the endoscope can be moved by a known distance towards the target 150. The change of magnification number can be related to known motion to calibrate for the focal length. When the distance is known, the endoscope can be automatically advanced towards the cyst to cover the distance between the aspiration catheter (120) and the target 150 to a predefined distance for optimal aspiration (defined by the aspiration system). As the endoscope 102 reaches the desired distance, aspiration is started for minimal amount of time defined as distance/speed of aspiration. This can be repeated until the target 150 is appropriately processed.

Figure 5:
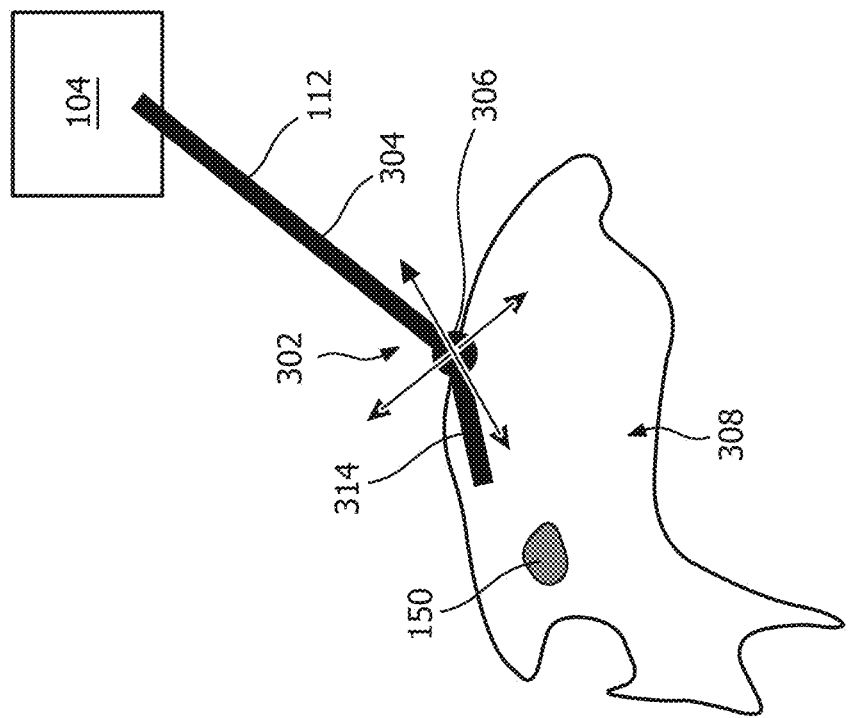
FIG. 5 is a diagram showing a robot system integrated with the endoscope to reposition a distal end of the endoscope in accordance with another embodiment.

Referring to FIG. 5, in another embodiment, an endoscope system 304 is implemented as a snake-like robot 302 with at least one joint 306 inserted into a body. In one embodiment, two concentric joints are controlled by two motors (not shown) to implement yaw and pitch motion of an endoscope tip 314. These two robot joints can be aligned with a structure 308 inside the body, such as third ventricle wall or heart wall, as a reference. The endoscope system 304 implements a channel in endoscope system 304, for a suction device, such as a catheter.

In another embodiment, the control of the endoscope system 304 may include joints 106, 107 (FIG. 3) that are controlled as a local RCM in the same fashion as a RCM robot (described above with reference to FIG. 3). The system 304 can optionally be combined with the RCM robot 104, where the RCM robot 104 controls external motion, and the snake-like robot 302 controls internal motion. The snake-like robot 302 can produce movement about a pivot point 306 and about its longitudinal axis. Other motions are also contemplated.

The present principles may be employed for endoscopic aspiration of unwanted formations in the body. The unwanted formations may include colloid cysts, blood clots, tumors or foreign objects in the heart or similar structures in kidneys, liver, or blood vasculature, etc. The aspiration may be performed by controlling the motion of a needle, endoscope, catheter or any other suitable instrument.

Figure 6:
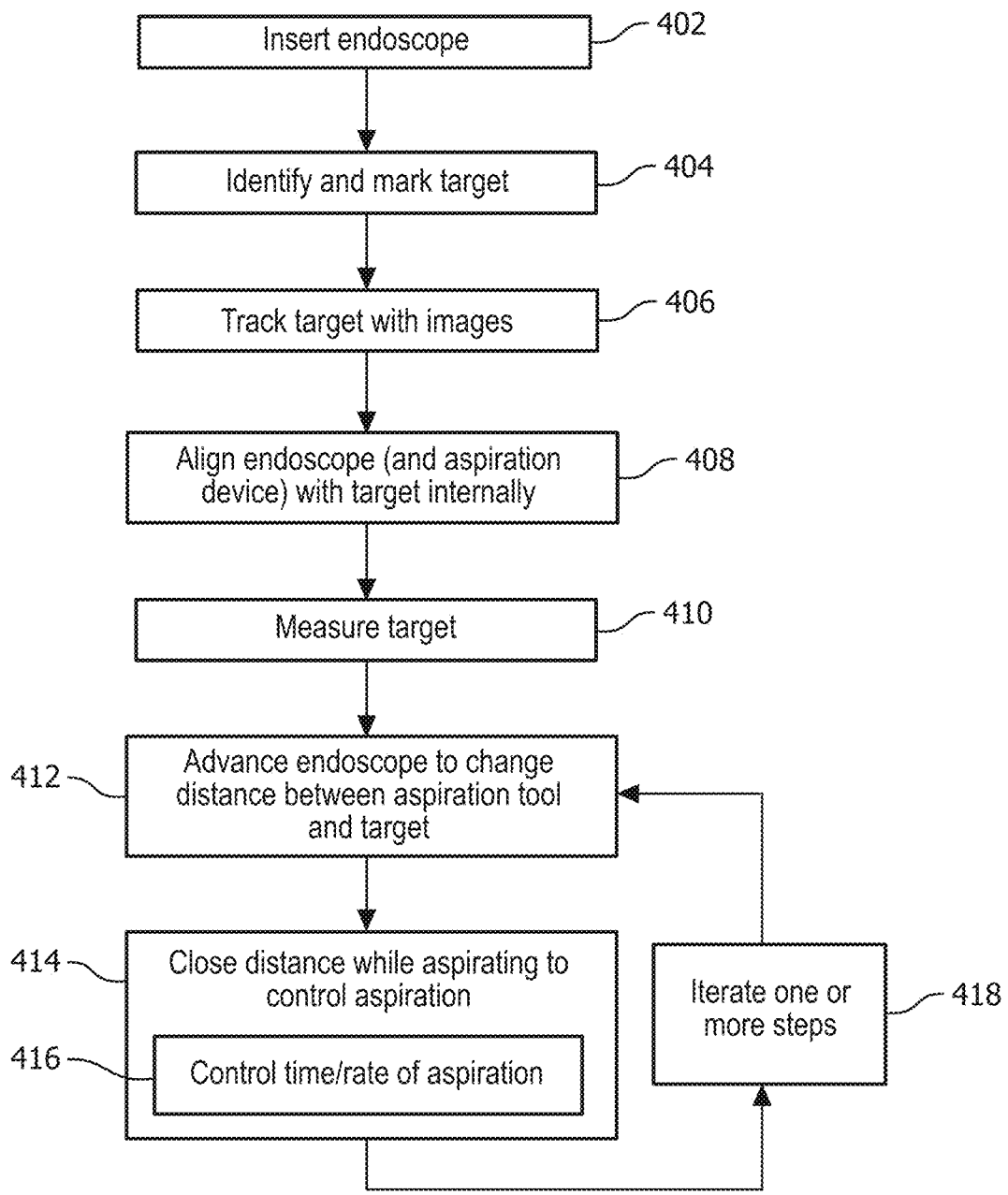
FIG. 6 is a flow diagram showing methods for aspiration using a robot system in accordance with illustrative embodiments.

Referring to FIG. 6, methods for treatment of tissue using a robot system are shown in accordance with the present principles. The methods will illustratively refer to aspiration of a cyst, but are applicable to any treatment method for any tissue. In block 402, an endoscope with a treatment device (e.g., an aspiration catheter) is inserted into an area of interest. In one embodiment, the endoscope is an end effector of a robot system. The robot system may include a mechanical remote center of motion configuration including at least one joint and at least two links to limit motion of the aspiration device at the insertion point into the subject to permit access to the target within the subject while minimizing contact with the subject at the insertion point. In other embodiments, the robot system is integrated within the endoscope (e.g., joints at the distal end portion to permit rotational adjustment of the endoscope and/or the aspiration device).

In block 404, a target is identified and marked in endoscope images. In block 406, the target is tracked with the treatment device (e.g., aspiration catheter) using image-based tracking. The image-based tracking may include one of optical flow or normalized cross-correlation tracking.

In block 408, the endoscope (and the aspiration catheter) is/are aligned with the target such that the endoscope is pivoted around an insertion point into a subject. The robot system limits motion to avoid unnecessary contact with the area around the insertion point. The aligning of the endoscope and the aspiration catheter with the target may include fitting a shape around edges of the target, computing a magnification from an endoscope view and a preoperative image and computing the distance between the aspiration catheter and the target.

In block 410, the target is measured in an endoscope view to determine a position or distance between the aspiration device and the target. Magnification (m=radius of the target in the endoscope view (in pixels)/radius of the target from preoperative images) is determined to find the distance between the endoscope tip (and aspiration catheter) and the target. This can be computed as: distance=m*f where f is the focal length of the endoscope lens. If the focal length of the endoscope is not known, the endoscope can be moved by a known distance towards the target. The change of magnification number can be related to known motion to calibrate for the focal length.

In block 412, the endoscope is positioned (e.g., advanced, retracted, maintained, moved laterally, etc.) to change the position (distance) between the aspiration catheter and the target to a predefined distance for aspiration. In block 414, the predetermined distance is covered (in any direction while aspirating) to provide aspiration for a distance or speed of aspiration. In block 416, a time/rate of aspiration (e.g., pressure and duration) based on the position (e.g., distance) of the treatment device (aspiration catheter) relative to the target can be controlled. The distance or time may be employed to control the amount of aspiration as the aspiration device moves into or through the target (e.g., the cyst). The control system controls a pressure and duration of aspiration in accordance with a position of the aspiration device and the target region. The control system limits treatment to only a region identified in the target region.

In block 418, one of more steps can be iterated to complete aspiration of the target. In one embodiment, automatic deployment of the aspiration device results in short bursts of aspiration as the aspiration device is advance and retracted through the cyst or target. The deployment is controlled based on images and knowledge of how far the robot and the aspiration device are from the target. The speed and rate of aspiration can be optimized to efficiently remove the cyst.

Figure 7:
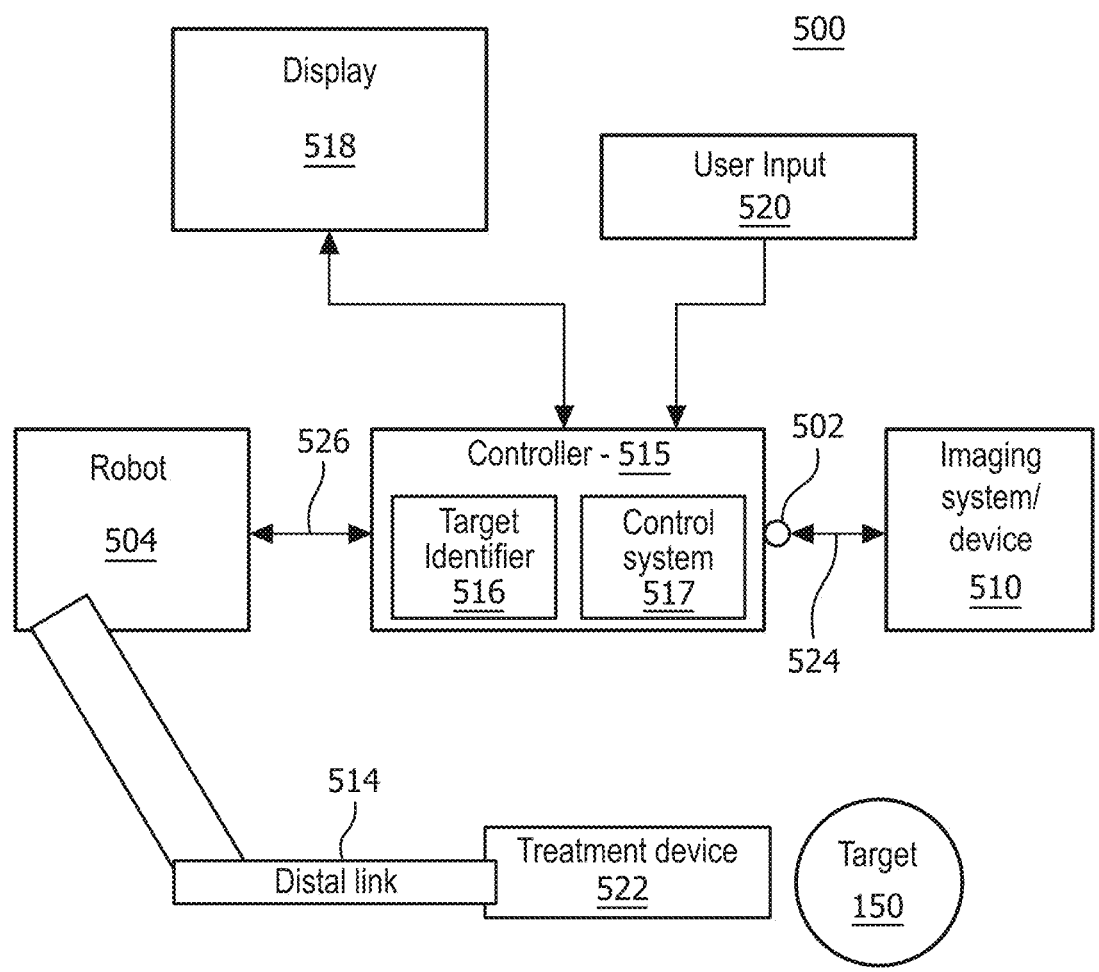
FIG. 7 is a block/flow diagram showing a controller to control motion of a robot in accordance with another embodiment.

Referring to FIG. 7, a system 500 having a controller 515 is shown in greater detail in accordance with one embodiment. The controller 515 may be an independent unit assembled with other components or may be part of a workstation 112 (FIG. 1), as with control system 115 (FIG. 1). The controller 515 receives images of an area of interest at one input 502 from an imaging device 510, such as an endoscope or other camera device or x-ray imaging device. The images 524 are provided to the controller 515, which can display the display images on a display device 518. The controller 515 also receives input from a clinician indicative of a target (e.g., the clinician selects one or more targets in the images 524). The input may be provided using an interface device 520 (computer keyboard, etc. (see interface 127, FIG. 1)). The target can be delineated in the image itself (e.g., circled or otherwise digitally distinguished) using a target identification device 516. The target identification device 516 defines a position in the image where the user has identified the target. The target identification device 516 may also permit the user to draw a shape (circle), etc. around the target so that the target is easily seen in displayed images.

One or more targets are tracked using image-based tracking based on images 524 received from the imaging device 510. These include real-time images, but can include fused or registered preoperative images as well. The controller 515 includes a control system 517 coupled to a robot 504 to generate control signals for moving the robot 504. The control signals are generated based upon bringing the target into an image field of view and then estimating a distance to the target 150.

The controller 515 sends a movement signal 526 to the robot 504 to articulate the robot 504 to position a distal link 514 of the robot 504. The robot 504 holds an aspiration device 522 or other device (e.g., laser for laser cutting, ablation electrode (e.g., RF or microwave), cauterizing apparatus, electroporation device, histotripsy device, high intensity focused ultrasound probe, etc.). The spatial relationship between the aspiration device 522 and a camera (endoscope) and the robot 504 is known; therefore, movement of the robot 504 accurately controls the movement of the aspirator 522 and an associated camera or imaging device. The controller 515 guides the robot motion along an approach axis so that the target can be imaged using the endoscope. The camera image provides positional feedback to lock in on the target 150.

From the images 524, the controller 515 can determine the size (volume) of the target and a distance from the target to the distal link 514 of the robot 504 based on images 524. If needed, the robot 504 is articulated along the approach axis to a start position based on the therapy device operational performance. The robotic motion is controlled by the controller 515, which limits the distance and angle of the aspiration device (or other treatment device) to limit the treatment regions specifically to that of the target (e.g., cyst, etc.). The therapy (e.g., aspiration) is performed based on known size and position of the target (to limit damage/fluid removal, among other things). The target area being delimitated and well defined permits the robot movement to be well-controlled within the specific target region as defined in the images 524.

Imaging continues throughout the process to update the size and/or shape and position of remaining portion or portions of the target. Changes may be made to the robot articulation based on changes that occur during treatment (in real-time or sequentially). The treatment continues with robotic placement of the treatment device 522 with image feedback from imaging device 510. The treatment or aspiration can be continuous based on the observed distance and calculated volume, or where aspiration is in bursts, based on a maximum aspiration volume per burst. The process is repeated, as needed, until imaging indicates that procedure is complete or a satisfactory result achieved.

In interpreting the appended claims, it should be understood that:
a) the word "comprising" does not exclude the presence of other elements or acts than those listed in a given claim;
b) the word "a" or "an" preceding an element does not exclude the presence of a plurality of such elements;
c) any reference signs in the claims do not limit their scope;
d) several "means" may be represented by the same item or hardware or software implemented structure or function; and
e) no specific sequence of acts is intended to be required unless specifically indicated.

Having described preferred embodiments for an image guided robotic system for tumor aspiration (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A robot controller comprising:
a memory; and
at least one processor coupled to the memory and configured to:
receive from an imaging device images of a region of interest,
identify at least one target region in the images,
generate control signals to control a robot configured to move a treatment device comprising an aspiration device within the region of interest, wherein the control signals are generated to control the robot to position the aspiration device a predefined distance to the at least one target region,
determine pressure of aspiration by the aspiration device based on the predefined distance of the positioned aspiration device to the at least one target region, wherein the predefined distance is greater than zero, and
control aspiration by the aspiration device based on the determined pressure of aspiration, wherein the at least one processor is configured to control the aspiration device based on a plurality of non-zero values for the pressure of aspiration as determined based on the pre-defined distance.

2. The robot controller as recited in claim 1, wherein the imaging device includes an endoscope having an instrument channel and the treatment device includes a catheter disposed within the instrument channel.

3. The robot controller as recited in claim 1, wherein the at least one processor is configured to guide the treatment device based on endoscopy images and preoperative images.

4. The robot controller as recited in claim 1, wherein the at least one processor is configured to enable a user to select the at least one target region and visually identify the selected at least one target region in the images.

5. The robot controller as recited in claim 1, wherein the at least one processor is configured to control the treatment device such that axes of at least one joint of the robot controlling the treatment device and a longitudinal axis of the treatment device substantially-coincide at an insertion point.

6. The robot controller, as recited in claim 1, wherein the at least one processor is configured to control at least one of a pulse width, duration, speed, and an amount of aspiration based on the predefined distance of the positioned aspiration device to the at least one target region.

7. The robot controller, as recited in claim 1, wherein the at least one processor is configured to compute the position of the aspiration device based on a magnification of an image of the at least one target region.

8. A treatment system comprising:
a treatment device comprising an aspiration device;
a robot configured to move the treatment device and position the aspiration device within at least one target region; and
a controller coupled to the robot, the controller configured to:
receive images from an imaging device for a region of interest,
identify the at least one target region in the images,
generate control signals to control the robot to position the aspiration device a predefined distance to the at least one target region,
determine pressure of aspiration by the aspiration device based on the predefined distance of the positioned aspiration device to the at least one target region, wherein the predefined distance is greater than zero, and
control aspiration by the aspiration device based on the determined pressure of aspiration, wherein the at least one processor is configured to control the aspiration device based on a plurality of non-zero values for the pressure of aspiration as determined based on the pre-defined distance.

9. The treatment system, as recited in claim 8, wherein the imaging device include an endoscope having an instrument channel and the aspiration device includes a catheter disposed within the instrument channel.

10. The treatment system as recited in claim 9, further comprising a joint disposed on a distal end of the endoscope to permit rotational motion of the endoscope.

11. The treatment system, as recited in claim 9, wherein the robot includes a distal link configured to secure the aspiration device such that axes of at least one joint of the robot and a longitudinal axis of the aspiration device coincide at an insertion point into a subject.

12. The treatment system as recited in claim 11, wherein the controller is configured to compute the position based on a magnification of an image of the at least one target region.

13. The treatment system as recited in claim 8, wherein the at least one processor is configured to control at least one of a pulse width, duration, speed, and an amount of aspiration based on the predefined distance of the positioned aspiration device to the at least one target region.

14. A non-transitory computer-readable storage medium having stored a computer program comprising instructions, which, when executed by a processor, cause the processor to:
  receive, from an imaging device, images of a region of interest;
  identify at least one target region in the images;
  generate control signals to control a robot configured to move a treatment device comprising an aspiration device within the region of interest, wherein the control signals are generated to control the robot to position the aspiration device a predefined distance to the at least one target region for aspiration;
  determine pressure of aspiration by the aspiration device based on the predefined distance of the positioned aspiration device to the at least one target region, wherein the predefined distance is greater than zero; and
  control aspiration by the aspiration device based on the determined pressure of aspiration, wherein the at least one processor is configured to control the aspiration device based on a plurality of non-zero values for the pressure of aspiration as determined based on the pre-defined distance.

15. The non-transitory computer-readable storage medium as recited in claim 14, wherein the control signals are generated to constrain motion of the robot controlling the treatment device at a software remote center of motion.

16. The non-transitory computer-readable storage medium as recited in claim 14, wherein the instructions, when executed by a processor, further cause the processor to enable a user to select the at least one target region and visually identifying the selected at least one target region in the images.

17. The non-transitory computer-readable storage medium, as recited in claim 14, wherein the instructions, when executed by a processor, further cause the processor to control at least one of a pulse width, duration, speed, and an amount of aspiration based on the predefined distance of the positioned aspiration device to the at least one target region.

18. The treatment system as recited in claim 8, wherein the controller is configured to guide the treatment device based on endoscopy images and preoperative images.

19. The treatment system as recited in claim 8, wherein the imaging device includes an endoscope having an instrument channel and the treatment device includes a catheter disposed within the instrument channel.

20. The non-transitory computer-readable storage medium of claim 14, wherein the instructions, when executed by a processor, further cause the processor to guide the treatment device based on endoscopy images and preoperative images.

* * * * *